(12) United States Patent
Busch

(10) Patent No.: US 7,490,987 B2
(45) Date of Patent: Feb. 17, 2009

(54) METHOD AND SYSTEM FOR OPTIMIZING RADIATION EXPOSURE FOR MEDICAL IMAGING EQUIPMENT

(75) Inventor: Erik Busch, Malvern, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 64 days.

(21) Appl. No.: 11/448,546

(22) Filed: Jun. 7, 2006

(65) Prior Publication Data
US 2007/0286346 A1 Dec. 13, 2007

(51) Int. Cl.
G01D 18/00 (2006.01)
H05G 1/44 (2006.01)
(52) U.S. Cl. ........................................ 378/207; 378/108
(58) Field of Classification Search ...................... 378/4, 378/19, 108, 162, 165, 65, 207
See application file for complete search history.

(56) References Cited

U.S. PATENT DOCUMENTS

| 5,621,779 | A  | * | 4/1997 | Hughes et al. ................. 378/65 |
| 7,031,423 | B2 | * | 4/2006 | Tsukagoshi .................... 378/4 |
| 2007/0016014 | A1 | * | 1/2007 | Hara et al. ................... 600/426 |
| 2007/0076842 | A1 | * | 4/2007 | Tkaczyk et al. ................ 378/5 |

* cited by examiner

Primary Examiner—Irakli Kiknadze
(74) Attorney, Agent, or Firm—Alexander J. Burke; Peter L. Kendall

(57) ABSTRACT

A system and method are provided for optimizing the amount of radiation exposure to a patient. The system and method comprise inputting a set of parameters based on characteristics of the patient, positioning components of a medical imaging equipment, comparing the input parameters and position of the components to computed optimum parameters and positions, and providing an indication of an amount of radiation dosage to be dispensed based on at least one of the input parameters and the position of the components.

30 Claims, 3 Drawing Sheets

METHOD AND SYSTEM FOR OPTIMIZING RADIATION EXPOSURE FOR MEDICAL IMAGING EQUIPMENT

BACKGROUND

1. Field of the Invention

The present invention is generally directed to medical imaging. More particularly, the present invention is directed to a method and system for optimizing the radiation dose to a user and/or an operator via medical imaging equipment.

2. Background of the Invention

For medical x-ray examinations in angiography and cardiology, excellent image quality is of particular importance in order to be able to differentiate clearly between the comparatively weakly absorbing structures being examined, in particular tissue and vessels as well as any catheters and stents present, in the body of a patient. At the same time, however, care must be taken to ensure that the patient and the medical personnel are exposed to as low an x-ray dose as possible.

The quality of a medical x-ray image depends on a large number of adjustable parameters. These parameters include, on the one hand, recording parameters, i.e. parameters such as those affecting the recording conditions obtained during imaging. These include in particular the voltage and current density of the supply voltage for the x-ray radiator as well as the exposure time and the setting of an x-ray filter. The quality of an x-ray image is additionally affected by variables generally dictated by the examination conditions. These include in particular the patient's thickness, i.e. the thickness of the irradiated body tissue, the radiator/detector spacing (also known as the source-image distance, or SID for short), the density of the patient, the frame rate, the angulation of the x-ray beam, and the x-ray photon energy level.

Recently, instead of conventional radiography employing x-ray films, digital x-ray diagnostic techniques in which the recorded x-ray image is present in electronic format, i.e. in the form of digital image data, have found widespread use. This makes it possible for the x-ray image to be post-processed using electronic image processing means before it is displayed on a screen. For a digital x-ray device it is therefore necessary to adjust not only the recording parameters but also a number of image processing parameters which affect the way in which the image is post-processed by the x-ray equipment and in turn the image quality.

It is known to control the recording parameters as a function of measurable input variables, e.g. the detector input dose, in such a way that comparable image quality is achieved under different examination conditions. For an x-ray device of this kind, a parameter configuration in which characteristics of the recording parameters are stored as a function of the input variables is generally predefined. These characteristics have hitherto been determined by the manufacturer on the basis of phantom measurements or simulation calculations.

The problem here is that the image quality and radiation dose do not constitute an objectively measurable variable, but are subject to the subjective impression of the treating radiologist. The visual impression expected and experienced as optimum is largely dictated by the experience or style of an x-ray department or even by the trained knowledgeability of an individual radiologist and therefore generally differs considerably from radiologist to radiologist.

Changing the parameter configuration of an x-ray device has hitherto been performed by technical support staff, especially as the x-ray equipment user, i.e. the treating physician, generally may not have full knowledge of all the available parameters at all times. Adapting the parameter configuration to suit the individual user would therefore involve considerable cost and/or complexity, particularly as different parameter configurations would also have to be provided as part of so-called organ programs for each body organ to be recorded, each recording projection and possibly different objects to be detected (body tissue, vessels or artificial implants such as catheters or stents), and this does not therefore usually take place.

As previously discussed, the radiologist may use her personal experience to set the parameters for the medical equipment. This can result in a situation where the radiation dose is too much which is harmful to the patient and the radiologist or anyone else in the room. For example, too much radiation can result in radiation burns for the patient.

In contrast, if the radiation dose is too low, a poor image may result. This may subject the patient and the radiologist to additional radiation exposure to acquire an adequate image. The end result in both situations is that the full capability of the medical imaging equipment is not utilized and suboptimal performance is achieved.

In addition, refinements in imaging equipment have improved image quality while reducing x-ray dose rates. However, even though technological progress has reduced exposure rates, the greater exposure duration that attends more complex procedures may lead to an increased overall patient and operator exposure accompanied by a greater potential for radiation induced injury.

A need exists for a medical imaging device that provides an adequate amount of radiation dosage that limits exposure to the patient and operating personnel.

A need also exists for a medical imaging device that provides feedback that allows operating personnel to know when they are providing suboptimal parameters to the system.

A need also exists for a medical imaging device that positions the components of the medical imaging device to achieve optimal radiation exposure by maintaining diagnostic image quality.

SUMMARY OF THE INVENTION

It is therefore an object of the present invention to provide a system and method where a patient and user are not over exposed to radiation. Preferably, this is accomplished in a manner in which optimum radiation exposure is provided to allow quality images to be acquired.

A system and method for optimizing the amount of radiation exposure to a patient are provided. The system and method comprise inputting a set of parameters based on characteristics of the patient, positioning components of a medical imaging equipment, comparing the input parameters and position of the components to computed optimum parameters and positions, and providing an indication of an amount of radiation dosage to be dispensed based on at least one of the input parameters and the position of the components.

In an aspect of the present invention, a medical imaging device provides an adequate amount of radiation dosage that limits exposure to the patient and operating personnel.

In another aspect of the present invention, a medical imaging device provides feedback that allows operating personnel to know when they are providing suboptimal parameters.

In still another aspect of the present invention, a medical imaging device positions the components of the medical imaging device to achieve optimal radiation exposure by maintaining diagnostic image quality.

In another aspect of the present invention, an indication includes at least one of a numerical value, a visual feedback comprising color coded graph and bar graph and a hard copy comprising a print out comprising a paper document to indicate the radiation exposure to the patient.

In a further aspect of the present invention, the components of the medical imaging device are positioned manually.

In a further aspect of the present invention, the components of the medical imaging device are positioned by motor.

BRIEF DESCRIPTION OF THE DRAWINGS

A wide array of potential embodiments can be better understood through the following detailed description and the accompanying drawings in which.

In the drawings, the same or similar elements are denoted by the same reference numerals even though they are depicted in different drawings.

DETAILED DESCRIPTION OF EXEMPLARY EMBODIMENTS

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
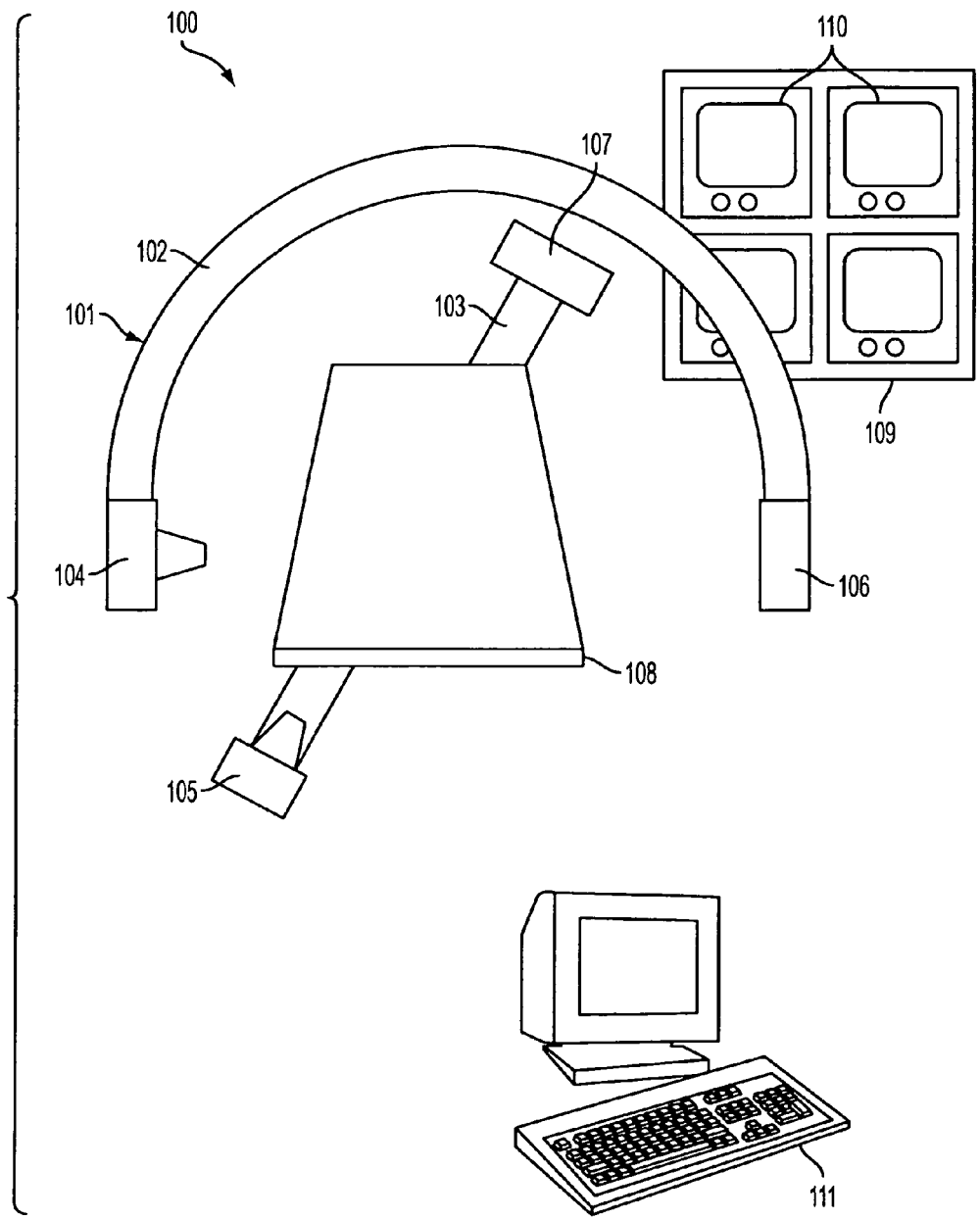
FIG. 1 is a diagram illustrating an exemplary medical imaging device in accordance with an embodiment of the present invention.

FIG. 1 is a diagram illustrating an exemplary medical imaging device 100 in accordance with an embodiment of the present invention. The medical imaging device comprises two C-arms 102 and 103, at the respective ends of which X-ray emitters 104 and 105 as well as X-ray detectors 106 and 107 situated opposite to each other in a known fashion. For example, flat detectors are installed.

It should be appreciated by those skilled in the art that the present invention can be performed without C-arms without departing from the scope of the present invention. For example, any medical imaging device having an emitter and detector can be used.

In addition, the medical imaging device 100 is provided with a patient examination table 108. For observation of the examination, a monitor support or monitor bank 109 is provided, in this example containing four monitors 110. However, a conventional medical imaging device 100 comprises at least one display.

An operating console 111 is located in an adjacent control room for communication with the system for the purpose of controlling the C-arms 102 and 103 and/or X-ray emitters 104 and 105 as well as X-ray detectors 106 and 107, image generation and image processing. Typically, an operating console 111 in the control room is provided with at least two monitors.

The C-arms 102 and 103 can be ceiling mounted and/or floor mounted. A combination of floor and ceiling mounted C-arms allows for adaptable positioning of the medical imaging device and fast programmable movement. It also allows peripheral examinations to be performed without repositioning a patient.

Characteristics that can play a role in the amount of radiation exposure are the age, gender, height, thickness, density and weight of the patient, area of the body being examined, the object being examined, and the like.

Further characteristics that can play a role in the amount of radiation exposure are the angle of the radiation beam, the video frame rate, the position of the radiation transmitter to the patient's body, and the radiation rate. It is well known in the art how these factors impact radiation. Therefore a detailed description of the affect of these factors on a patient's body will not be described for conciseness.

It should be appreciated by those skilled in the art that the medical imaging device 100 is not limited to a specific type or field of medical imaging device. For example, an angiography system is shown for illustrative purposes only.

Figure 2:
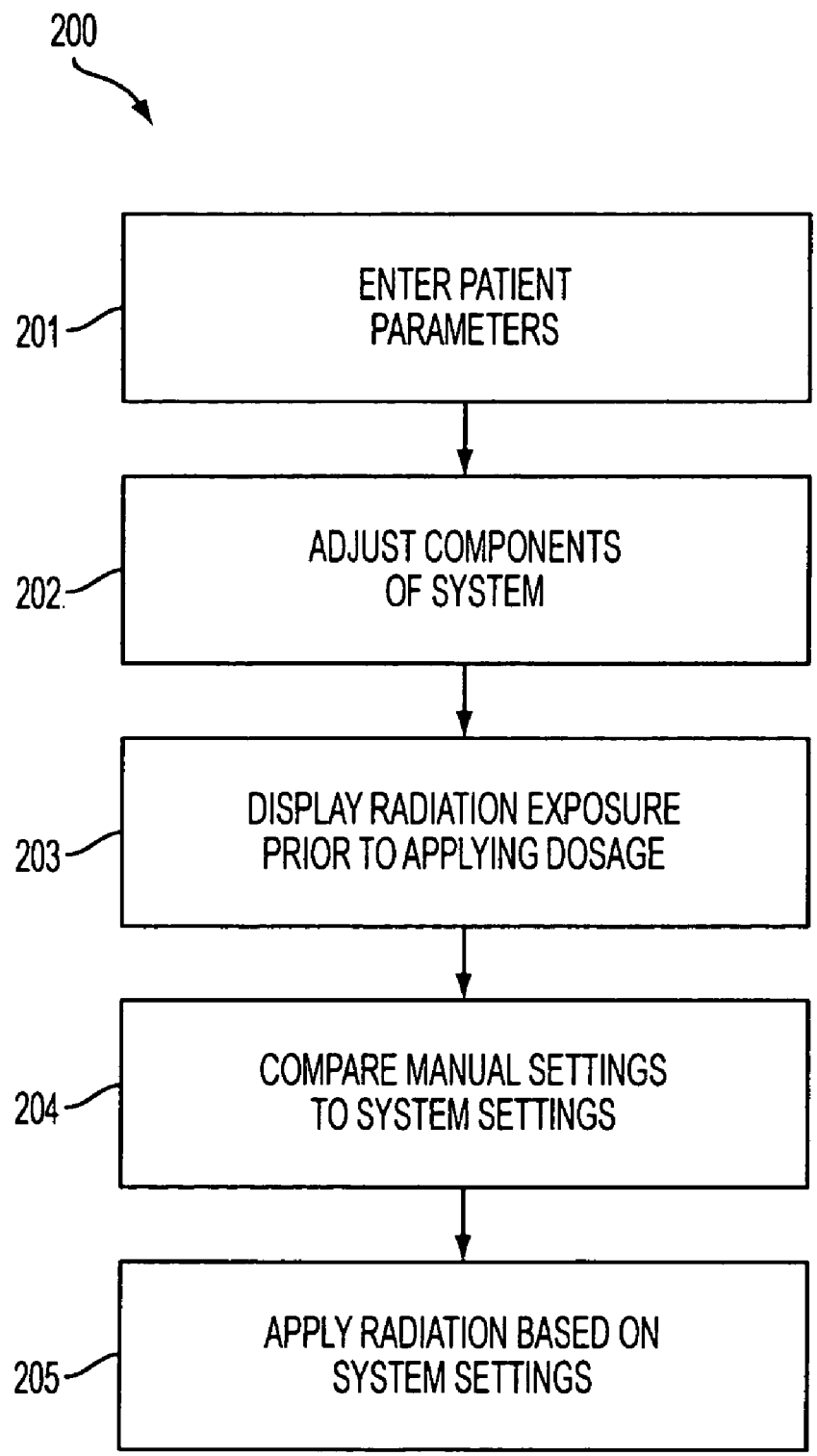
FIG. 2 is a flow chart illustrating a process for optimizing radiation exposure for medical equipment in accordance with an embodiment of the present invention.

FIG. 2 is a flow chart illustrating a process 200 for optimizing radiation exposure for medical equipment in accordance with an embodiment of the present invention. Specifically, the process adjusts the radiation settings to provide the optimum radiation dosage to achieve the optimum image.

At step 201, an operator enters a set of parameters based on a patient's gender, weight, height, area of the body to be examined, object to be examined and the like.

At step 202, the components of the system e.g., the table, collimators, copper filtration, detectors, and C-arms of the medical imaging device are adjusted manually accordingly. The term manually refers to the operator adjusting the components based on the operator's experience. The system can also be moved electronically and/or by motor under the direction of the operator. In this case, the term electronically is substantially the same as the term manually because both are based on the operator controlling the position of the components.

Specifically, the operator seeks to adjust the C-arm and transmitters to position the C-arm and receivers at an optimum position relative to the patient's body. If the receiver is too far away, or if the system adjusts the exposure automatically based on the entrance dose at a receptor then the patient may be exposed to significantly higher x-ray dose.

The angulation of the radiation beam also has to be taken into account. For example, if the angulation of the radiation beam is too steep (cranial caudal) a stronger radiation beam is required because the amount of patient anatomy between the transmitter and receiver. In addition, this leads to more radiation exposure for the patient as well as possible radiation burns. The operator is also at a potential risk due to the additional radiation exposure.

The frame rate and radiation rate can also be set by the operator. This increases the number of factors that affect the amount of radiation the patient is subject to.

At step 203, the operator can determine the amount of radiation exposure the patient may be subject to based on the operator's settings and the position of the components prior to radiation being applied. The indication provided can comprise at least one of a numerical value, a visual feedback comprising a bar graph and a color coded chart and a print out comprising a paper document to indicate the radiation exposure and/or radiation dosage. The indication can be provided on a display comprising a cathode ray tube, a plasma screen and/or a liquid crystal display.

In an embodiment of the present invention, a warning indication can also be provided if the amount of radiation is above a threshold value. For example, if the amount of radiation can lead to radiation burns or radiation exposure to the operator an audible alarm or visual alarm can be provided. The audible alarm can comprise a siren, bell and the like. The visual alarm can comprise a strobe light, light emitting diodes, colored lights and the like.

At step 204, the operator can determine optimal settings for the medical imaging device 100 by having the medical imaging device 100 determine its optimal settings based on characteristics of the patient. In an embodiment of the present invention, input parameters and the manual settings are compared to the manufacturer's settings comprising computed optimum parameters and positions.

The components are then positioned by motor and/or electronically under the control of the medical imaging system or can be controlled manually whereby the operator is instructed where to position the components.

In an embodiment of the present invention, the indication for indicating the amount of radiation dosage and/or radiation exposure can be a comparison between the manual settings and manual position of the components of the medical imaging device 100 and the manufacturer's computed optimum parameters and positions of the components of the medical imaging device 100 based on system detection of a patient's characteristics. For example, an auto detect feature can be used to detect the characteristics of the patient's body. Optimum search algorithms and sensor/user feedback can be used to achieve this.

By showing a comparison between the manual settings and computed optimum parameters and positions, the indication for providing an amount of radiation dosage prior to the radiation dosage being applied can be used as a training tool. The operator or manager of the operator can use the knowledge gained to seek training for the operator or to monitor the operator's progress.

In another embodiment of the present invention, preset images can be shown on the display showing how the images would appear. For example, an image that is blurred can be used to show an inadequate radiation dosage. An image based on the computed optimum parameters and positions can be used to show how an optimum amount of radiation can produce an optimum image.

At step 205, after determining that the indication levels of the radiation dosage are acceptable, the operator can accept the levels, apply the radiation dosage to the patient and view the image taken.

It should be appreciated by those skilled in the art that step 201 can be eliminated without departing from the scope of the present invention. Some older medical imaging systems may require the input of patient parameters rather than auto detecting the patient parameters.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 3:
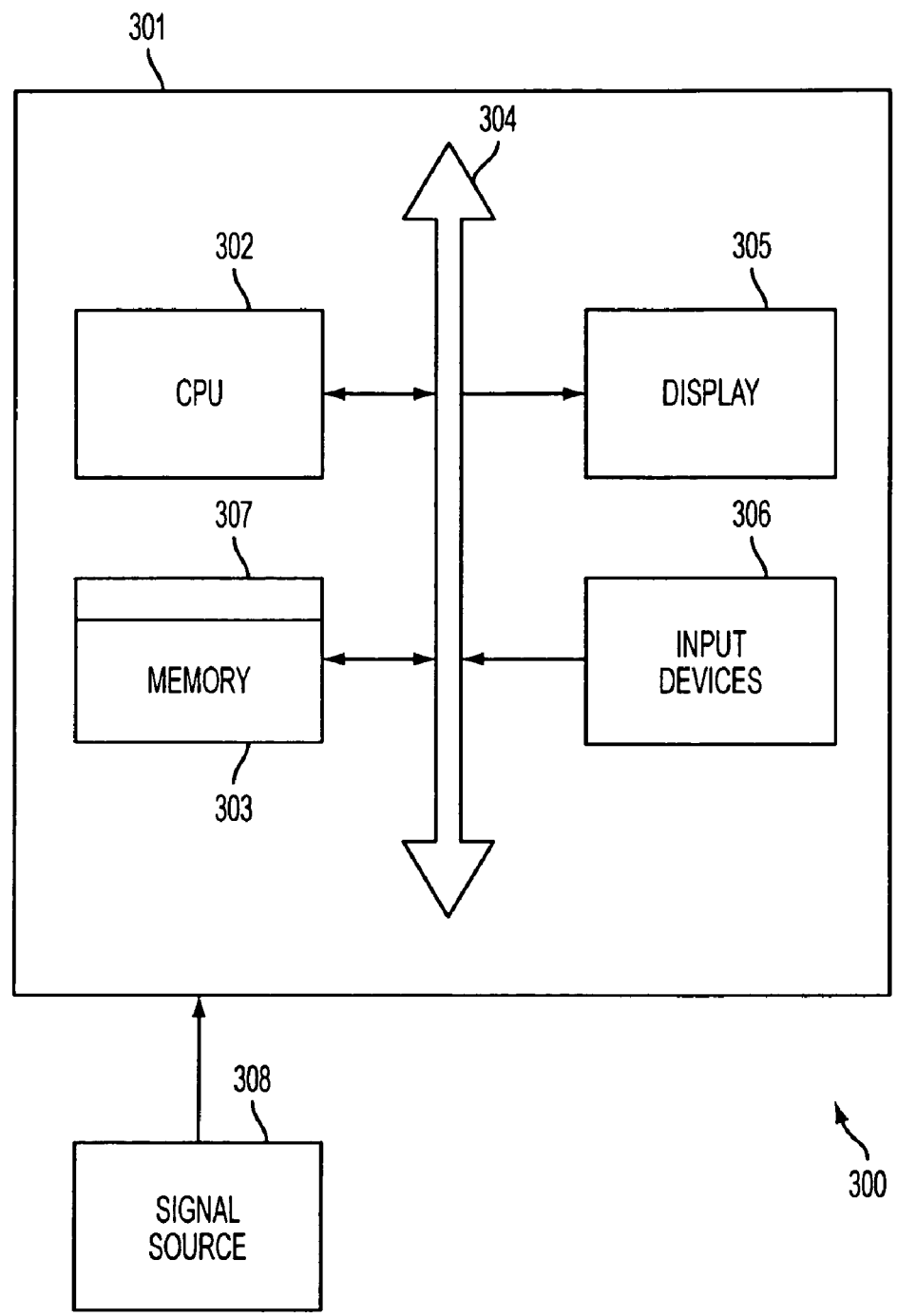
FIG. 3 is a block diagram of a computer for optimizing radiation exposure in accordance with an embodiment of the present invention.

Referring now to FIG. 3, according to an embodiment of the present invention, a computer system 301 for implementing the present invention can comprise, inter alia, a central processing unit (CPU) 302, a memory 303 and an input/output (I/O) interface 304. The computer system 301 is generally coupled through the I/O interface 304 to a display 305 and various input devices 306 such as a mouse and a keyboard. The support circuits can include circuits such as cache, power supplies, clock circuits, and a communication bus. The memory 303 can include random access memory (RAM), read only memory (ROM), disk drive, tape drive, etc., or a combinations thereof. The present invention can be implemented as a routine 307 that is stored in memory 303 and executed by the CPU 302 to process the signal from the signal source 308. As such, the computer system 301 is a general purpose computer system that becomes a specific purpose computer system when executing the routine 307 of the present invention.

The computer system 301 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for optimizing the amount of radiation exposure to a patient, the method comprising:
    inputting a set of parameters based on characteristics of the patient;
    positioning components of a medical imaging equipment;
    comparing the input parameters and position of the components to computed optimum parameters and positions; and
    providing an indication of an amount of radiation dosage to be dispensed based on at least one of the input parameters and the position of the components.

2. The method of claim 1, wherein the radiation dosage comprises x-rays.

3. The method of claim 1, further comprising:
    dispensing the radiation dosage if the amount of radiation dosage to be dispensed is acceptable; and
    displaying an image of the patient.

4. The method of claim 1, wherein the step of positioning further comprises:
    manually positioning the components.

5. The method of claim 1, wherein the step of positioning further comprises:
    electronically positioning the components by motor.

6. The method of claim 1 further comprising:
    selectively adjusting the components of the medical imaging device in accordance with the computed optimum parameters and positions.

7. The method of claim 1, wherein the components comprise at least one C-arm.

8. The method of claim 1, wherein the components comprise at least one detector.

9. The method of claim 1, wherein the components comprise a table.

10. The method of claim 1, wherein the components comprise at least one radiation emitter.

11. The method of claim 10, wherein the radiation emitter comprises at least one X-ray emitter.

12. The method of claim 1, further comprising:
selectively displaying preset images based on the position of the components and the computed optimum parameters and positions.

13. The method of claim 1, wherein the step of providing further comprises:
providing a color coded scale for indicating the amount of radiation dosage.

14. The method of claim 1, wherein the step of providing further comprises:
providing a visual feedback comprising a bar graph for indicating the amount of radiation dosage.

15. The method of claim 1, wherein the step of providing further comprises:
providing a numerical value for indicating the amount of radiation dosage.

16. A system for optimizing the amount of radiation exposure to a patient, comprising:
an input device for inputting a set of parameters based on characteristics of the patient;
a table for adjusting a position of the patient;
at least one C-arm having radiation emitters and detectors at opposing ends for transmitting and detecting radiation;
a processor for comparing the input parameters and position of the table and the at least one C-arm to computed optimum parameters and positions; and
a display for displaying an image indicative of the radiation exposure of the patient prior to the radiation dosage being applied.

17. The system of claim 16, wherein the image indicative of the radiation exposure of the patient prior to the radiation dosage being applied comprises at least one of a bar graph, a numerical value and a print out.

18. The system of claim 16, wherein the radiation emitter comprises an X-ray emitter.

19. The system of claim 16, wherein the system comprises a medical imaging device.

20. The system of claim 16, wherein the image indicative of the radiation exposure of the patient prior to the radiation dosage being applied comprises a color coded scale.

21. The system of claim 16, wherein the processor comprises an optimum search algorithm for optimizing system settings.

22. The system of claim 16 further comprising a memory.

23. The system of claim 22, wherein the memory stores the computed optimum parameters and positions.

24. The system of claim 16, wherein the memory is located at least one of remotely from the system or locally with the system.

25. The system of claim 16, wherein the computed optimum parameters and positions are selected by the system via an auto detect feature to determine characteristics of the patient.

26. A method for optimizing the amount of radiation exposure to a patient, the method comprising:
manually positioning components of a medical imaging equipment; and
providing an indication of an amount of radiation dosage to be dispensed based on the position of the components prior to applying the dosage.

27. The method of claim 26, wherein the radiation dosage comprises x-rays.

28. The method of claim 26, further comprising:
providing an alarm if the radiation dosage exceeds a threshold value.

29. The method of claim 26 further comprising:
selectively adjusting the components of the medical imaging device in accordance with computed optimum parameters and positions.

30. The method of claim 26, further comprising:
dispensing the radiation dosage if the amount of radiation dosage to be dispensed is acceptable; and
displaying an image of the patient.

\* \* \* \* \*